United States Patent
Beran et al.

[11] Patent Number: 6,074,363
[45] Date of Patent: Jun. 13, 2000

[54] INTRAVENOUS FLUID HEAT EXCHANGER

[75] Inventors: Anthony V. Beran, Santa Ana; Gordon Shigezawa, Irvine, both of Calif.

[73] Assignee: Respiratory Support Products, Inc., Irvine, Calif.

[21] Appl. No.: 08/924,613

[22] Filed: Sep. 5, 1997

[51] Int. Cl.[7] ........................................... A61F 7/12
[52] U.S. Cl. .................. 604/113; 607/104; 165/163; 165/165
[58] Field of Search ..................... 604/113, 114; 607/96–114; 165/46, 155, 156, 162, 163–165, 172, 173, 175, 176

[56] References Cited

U.S. PATENT DOCUMENTS

| | | |
|---|---|---|
| 4,249,923 | 2/1981 | Walda . |
| 4,476,685 | 10/1984 | Aid . |
| 4,532,414 | 7/1985 | Shah et al. . |
| 4,705,508 | 11/1987 | Karnavas et al. . |
| 4,962,761 | 10/1990 | Golden . |
| 5,106,373 | 4/1992 | Augustine et al. . |
| 5,154,661 | 10/1992 | Higgins . |
| 5,180,896 | 1/1993 | Gibby et al. . |
| 5,269,749 | 12/1993 | Koturov . |
| 5,579,836 | 12/1996 | Maruyama ............................ 165/175 |
| 5,649,588 | 7/1997 | Lee ........................................ 165/153 |
| 5,806,586 | 9/1998 | Osthues et al. ........................ 165/174 |
| 5,807,332 | 9/1998 | Augustine et al. ..................... 604/113 |

*Primary Examiner*—Ronald K. Stright, Jr.
*Attorney, Agent, or Firm*—Price Gess & Ubell

[57] ABSTRACT

An intravenous (IV) fluid heat exchanger which transfers heat from a heating medium to an intravenous fluid being delivered to a patient. The IV fluid heat exchanger includes an input manifold for receiving the IV fluid and distributing the IV fluid through a plurality of passageways extending from the input manifold. An output manifold is also provided for receiving the IV fluid flowing through the passageways and directing the IV fluid through an exit path out of the IV fluid heat exchanger. The passageways are positioned in the proximity of the heating medium, wherein the passageways facilitate the transfer of heat from the heating medium to the IV fluid passing through the passageways. By providing a plurality of passageways for the IV fluid, the surface area of the IV fluid exposed to the inner surfaces of the heated passageways is optimized to improve the heating efficiency of the IV fluid heat exchanger. A flow control unit may also be positioned within the input manifold for variably controlling the number of passageways which are opened to allow the flow of IV fluid there through in order to regulate the surface area of the IV fluid exposed to the inner surfaces of the passageways. In this manner, the amount of heat transferred to the IV fluid from the heating medium can be variably controlled.

1 Claim, 7 Drawing Sheets

INTRAVENOUS FLUID HEAT EXCHANGER

BACKGROUND OF THE INVENTION

1. Technical Field

The present invention relates generally to heating devices used for heating an intravenous fluid during delivery of the intravenous fluid to a patient in a hospital environment. More particularly, the present invention relates to an intravenous fluid heat exchanger used in conjunction with a heated gaseous fluid being delivered to an inflatable, thermal blanket covering a patient to warm intravenous fluid being administered to the patient.

2. Background Art

It is often desirable to control the temperature of a patient in a hospital setting to prevent a patient's body temperature from dropping below a desired temperature. In order to control the patient's body temperature, it is well known in the medical field to cover a patient with a thermal blanket having a temperature-controlled medium flowing there through to substantially surround the patient with a warm environment. One such thermal blanket is disclosed in U.S. Pat. No. 4,777,802 issued to Feher, where heated air is blown into a blanket used to cover a patient. The blanket includes an outer layer impermeable to air and an inner air-permeable layer, where the heated air passes through the inner air-permeable layer to flow over and heat the patient covered by the blanket.

In addition to the outer environment surrounding the patient, a further factor existing in controlling a patient's body temperature involves the administration of intravenous (IV) fluids to a patient in a hospital setting. Many IV fluids are conventionally stored in a cold atmosphere to preserve the IV fluids until they are used in a patient. The injection of cold IV fluids into a patient creates a major source of conductive heat loss within the patient, thus lowering the body temperature of the patient. Therefore, it is common in the medical field to heat IV fluids prior to intravenous injection of the IV fluids into the patient. Examples of such IV fluid heating techniques include immersing the IV fluid in a warm liquid bath or running the IV fluid through a carrier which rests upon an electrical hot plate. However, such prior IV fluid heating techniques are generally inefficient, expensive, or provide inaccurate temperature control of the IV fluid.

In an attempt to overcome some the problems present in prior IV fluid heating techniques, U.S. Pat. No. 5,106,373 issued to Augustine et al. discloses warming intravenously-administered fluids by passing a portion of an IV tube through a thermal blanket as described above having a heated gas flowing there through to warm the exterior of a patient. The portion of the IV tube located within the thermal blanket is positioned in the flow path of the heated gas traveling through the thermal blanket, where thermal energy is transferred from the heated gas to the IV fluid flowing through the thermal blanket. The portion of the IV tube traveling through the thermal blanket is designed to have the same diameter as the rest of the IV tube, so that the flow rate of the IV fluid is not altered as it travels through the portion of the IV tube in the thermal blanket. Since thermal blankets are often used in a hospital setting in order to regulate a patient's body temperature, incorporating an IV fluid warming device into a thermal blanket is quite desirable as it provides a simple, efficient, and cost-effective manner of heating IV fluid without the requiring additional equipment or procedures for warming the IV fluid.

However, the IV fluid warming device disclosed by Augustine et al. does not allow the temperature of the IV fluid to be adequately controlled for the specific requirements of each individual patient. The amount of warming provided to the IV fluid is dependent upon the temperature of the heated gas flowing through the thermal blanket and the surface area of the IV fluid exposed to the increased temperature of the heated gas, which is determined by the inner surface area of the IV tube extending through the thermal blanket. The inner surface area of the IV tube within the thermal blanket of Augustine et al. remains a constant value, so that it would be necessary to change the temperature of the heated gas flowing through the thermal blanket in order to variably control the amount of heat transferred to the IV fluid. However, changing the temperature of the heated to control the temperature of the IV fluid would interfere with system's primary function of heating the body of a patient. Further, in some instances, it is desirable to heat the outside of a person's body using the thermal blanket while only needing to partially heat the IV fluid passing though the thermal blanket. Whereas, the IV fluid warming device of Augustine et al. does not allow for separate control of the temperature of the IV fluid from the temperature of the heated gas passing through the thermal blanket.

Clearly, there is a need for an IV fluid heat exchanger which easily and effectively allows the temperature of the IV fluid to be precisely regulated. Further, there is a need for a temperature-controllable IV fluid heat exchanger which may be readily used in conjunction with a gaseous-heated thermal blanket for providing the heating medium for the IV fluid.

OBJECTS AND SUMMARY OF THE INVENTION

It is a primary object of the present invention to overcome the aforementioned shortcomings associated with the prior art.

Another object of the present invention is to provide an IV fluid heat exchanger which maximizes the amount of heat transferred to the IV fluid by maximizing the surface area of the IV fluid exposed to said heated gaseous fluid.

Yet another object of the present invention is to provide an IV fluid heat exchanger which easily and effectively allows the temperature of the IV fluid delivered to a patient to be precisely regulated.

A further object of the present invention is to provide an IV fluid heat exchanger which variably controls the surface area of the IV fluid exposed to the heating medium in order to control the amount of heat transferred to the IV fluid.

It is yet another object of the present invention to provide an IV fluid heat exchanger which uses a heated gaseous fluid supplied to a gaseous-heated thermal blanket as a heating medium for IV fluid to provide a simple and efficient manner of heating the IV fluid.

Still another object of the present invention to provide an IV fluid heat exchanger which utilizes electrical resistance as a heating medium to provide a versatile and easily transportable IV fluid heating device.

These as well as additional objects and advantages of the present invention are achieved by providing an intravenous (IV) fluid heat exchanger which transfers heat from a heating medium to an intravenous fluid flowing through the IV fluid heat exchanger. The IV fluid heat exchanger includes an input manifold having an opening for receiving IV fluid from an IV fluid source and a plurality of outlets for distributing the IV fluid through the IV fluid heat exchanger. A plurality of passageways extend from the input manifold, where each outlet in the input manifold is connected to a respective passageway. An output manifold is further provided having a plurality of inlets for receiving the IV fluid flowing through the passageways, wherein each inlet in the output manifold is connected to a respective passageway. The output manifold includes an aperture for providing an exit path directing the IV fluid out of the IV fluid heat exchanger.

In a preferred embodiment of the present invention, a flow of heated gaseous fluid is used as the heating medium. At least a portion of the passageways are positioned in the proximity of a flow of a heated gaseous fluid flowing into an inflatable, thermal blanket, wherein the passageways are formed of a thermally conductive material to facilitate the transfer of heat from the heated gaseous fluid to the IV fluid passing through the passageways. By providing multiple passageways for the IV fluid, the surface area of the IV fluid exposed to the inner surfaces of the passageways heated by the gaseous fluid is optimized to improve the heating efficiency of the IV fluid heat exchanger of the present invention.

In another preferred embodiment of the present invention, a flow control unit is positioned within the input manifold for variably controlling the number of passageways which are opened to allow the flow of IV fluid there through. By regulating the number of passageways which are open for IV fluid flow, the surface area of the IV fluid exposed to the inner surfaces of the passageways can also be variably controlled. In this manner, the amount of heat transferred to the IV fluid from the heated gaseous fluid can be controlled without adjusting the temperature of the heated gaseous fluid. In a preferred embodiment of the present invention, the flow control unit includes a syringe-type plunger assembly which is reciprocally actuable within the input manifold to control the number of passageways accessible by the intravenous fluid by sealing off all of the passageways on an opposite side of the plunger assembly from the side adjacent to the opening for the IV fluid source.

In order to maximize the amount of heat transferred to the IV fluid by maximizing the inner surface area of the passageways, the passageways may formed in a variety of shapes along the longitudinal direction of the passageways, including a linear shape, coiled shape, or serpentine shape. The IV fluid heat exchanger is preferably positioned directly in the flow path of the heated gaseous fluid flowing into the thermal blanket, such as within the supply tube introducing the heated gaseous fluid into the thermal blanket, within the thermal blanket itself, or within a housing which fluidically connects the supply tube to the thermal blanket. Alternatively, the IV fluid heat exchanger may be positioned adjacent to, but not directly within, the flow path of the heated gaseous fluid, such as on the outer surface of the thermal blanket adjacent to the flow path of the heated gaseous fluid within the thermal blanket.

In an alternative embodiment of the present invention, electrical resistance is used as the heating medium for the IV fluid. A conductive element, such as a conductive wire or a coating of electrically-conductive material, is formed around the row of passageways. An electrical current is run through the conductive element, where the resistance of the conductive element to the flow of current therethrough serves to heat the conductive element and, in turn, the row of passageways. The conductive element is juxtapositioned in close proximity to the row of passageways in order to provide an efficient transfer of heat to the IV fluid flowing through the passageways. The conductive element may be constructed in either a disposable or reusable form.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a simple and efficient heat transfer apparatus for an IV fluid.

Figure 1:
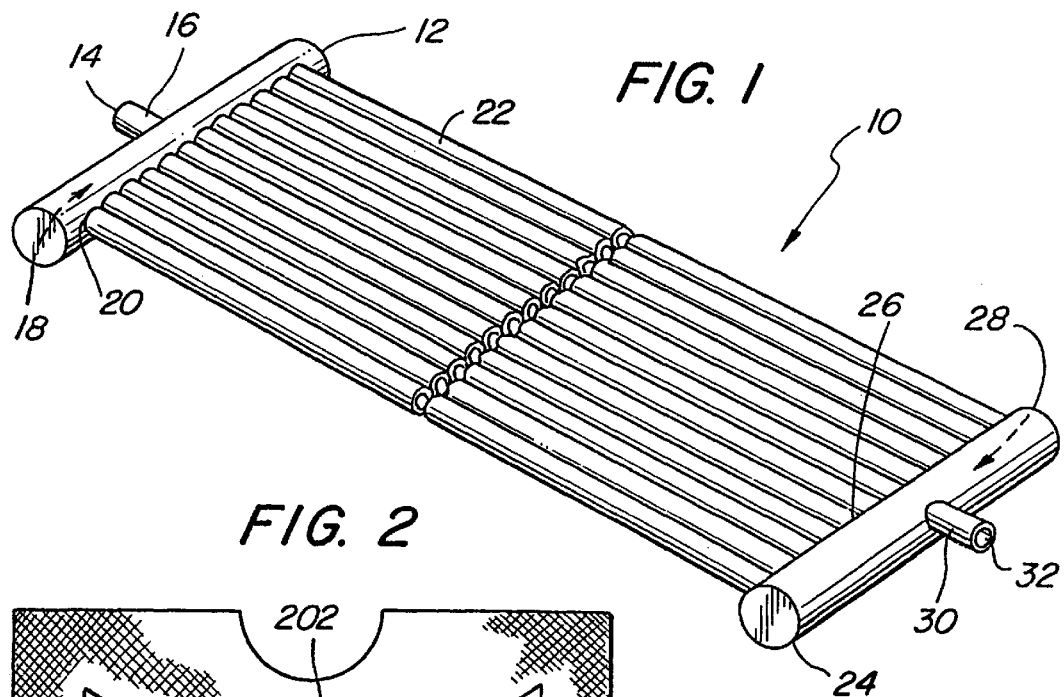
FIG. 1 is a perspective view of a preferred embodiment of the IV fluid heat exchanger of the present invention.

Referring now to FIG. 1, a perspective view of an IV fluid heat exchanger 10 in accordance with a preferred embodiment of the present invention is illustrated. The IV fluid heat exchanger 10 includes an input manifold 12 having an opening 14 for receiving an IV fluid from an IV fluid source. Opening 14 is preferably formed at the end of a protrusion 16 extending outwardly from an outer surface of input manifold 12, where protrusion 16 may be formed as a Luer lock or other similar device typically used for connection with an IV fluid tube. A central chamber 18 is provided within input manifold 12 for containing the IV fluid supplied to input manifold 12 through opening 14. Intake manifold 12 further includes a plurality of outlets 20 for distributing the IV fluid out of central chamber 18. A plurality of passageways 22 extend away from input manifold 12, where each outlet 20 in input manifold 12 is fluidically connected to a respective one of the passageways 22. Passageways 22 are preferably formed in the shape of tubular members. However, passageways 22 may be formed in any shape which provides adequate fluid flow characteristic for an IV fluid similar to that of tubular passageways 22. Central chamber 18 is fluidically connected with both opening 14 and passageways 22, so that the IV fluid supplied through opening 14 is collected within chamber 18 and then distributed through passageways 22.

The IV fluid heat exchanger further includes an output manifold 24 having a plurality of inlets 26 attached to passageways 22 for receiving the IV fluid flowing through passageways 22, where each inlet 26 is connected to a respective passageway 22. A collecting chamber 28 is provided within output manifold 24 for receiving the IV fluid flowing through passageways 22 into output manifold 24. A protrusion 30 (similar to protrusion 16) extends from output manifold 24 having an aperture 32 in fluidic communication with collecting chamber 28 for directing the IV fluid out of output manifold 24 and into an IV fluid tube delivering the output IV fluid to a patient.

In order to heat the IV fluid flowing through IV fluid heat exchanger 10, at least a portion of each passageway 22 is positioned in the proximity of a heated gaseous fluid flow path. The heated gaseous fluid functions as the heating medium for the IV fluid, where the heat from the heated gaseous fluid is transferred through passageways 22 to the IV fluid flowing within passageways 22. Passageways 22 are formed from a material having a high thermal conductivity to allow the heat from the heated gaseous fluid to travel through passageways 22 to the IV fluid flowing through passageways 22. While passageways 22 may be formed from any flexible, thermally conductive material, passageways 22 are preferably formed of a thermoplastic material or a thermoplastic material having metallic particles interspersed throughout the thermoplastic material. Since passageways 22 facilitate the transfer of heat from the heated gaseous fluid to the IV fluid, the amount of heat transferred to the IV fluid is dependent upon the amount of IV fluid exposed to the inner surface of passageways 22. Therefore, the heat exchanged from the heated gaseous fluid to the IV fluid is a function of the inner surface area and length of passageways 22 as well as the wall thickness of passageways 22. The IV fluid heat exchanger of the present invention employs multiple passageways 22 to maximize the amount of heat transferred to the IV fluid by maximizing the surface area of passageways 22 exposed to the IV fluid. The temperature of the IV fluid is therefore dependent upon the amount of IV fluid exposed to higher temperatures. By providing multiple passageways 22 for the IV fluid, the surface area of the IV fluid exposed to the inner surfaces of the heated passageways 22 is maximized to improve the heating efficiency of the IV fluid heat exchanger 10 of the present invention.

Figure 2:
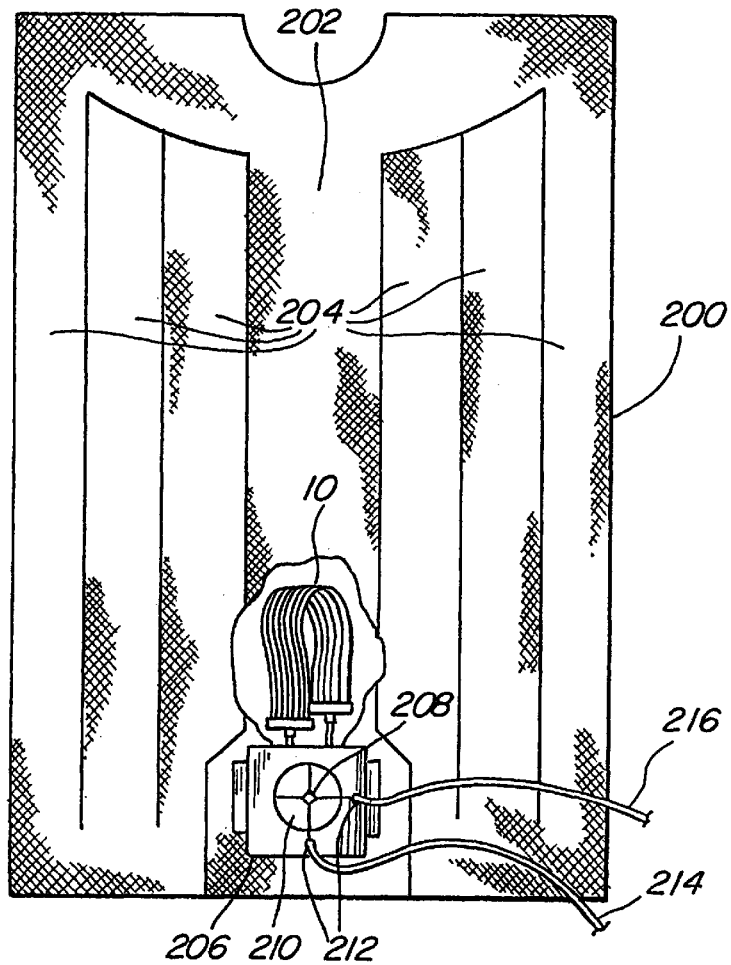
FIG. 2 is a partial cut-away top view of the IV fluid heat exchanger of FIG. 1 shown positioned within an inflatable, thermal blanket.
Figure 3:
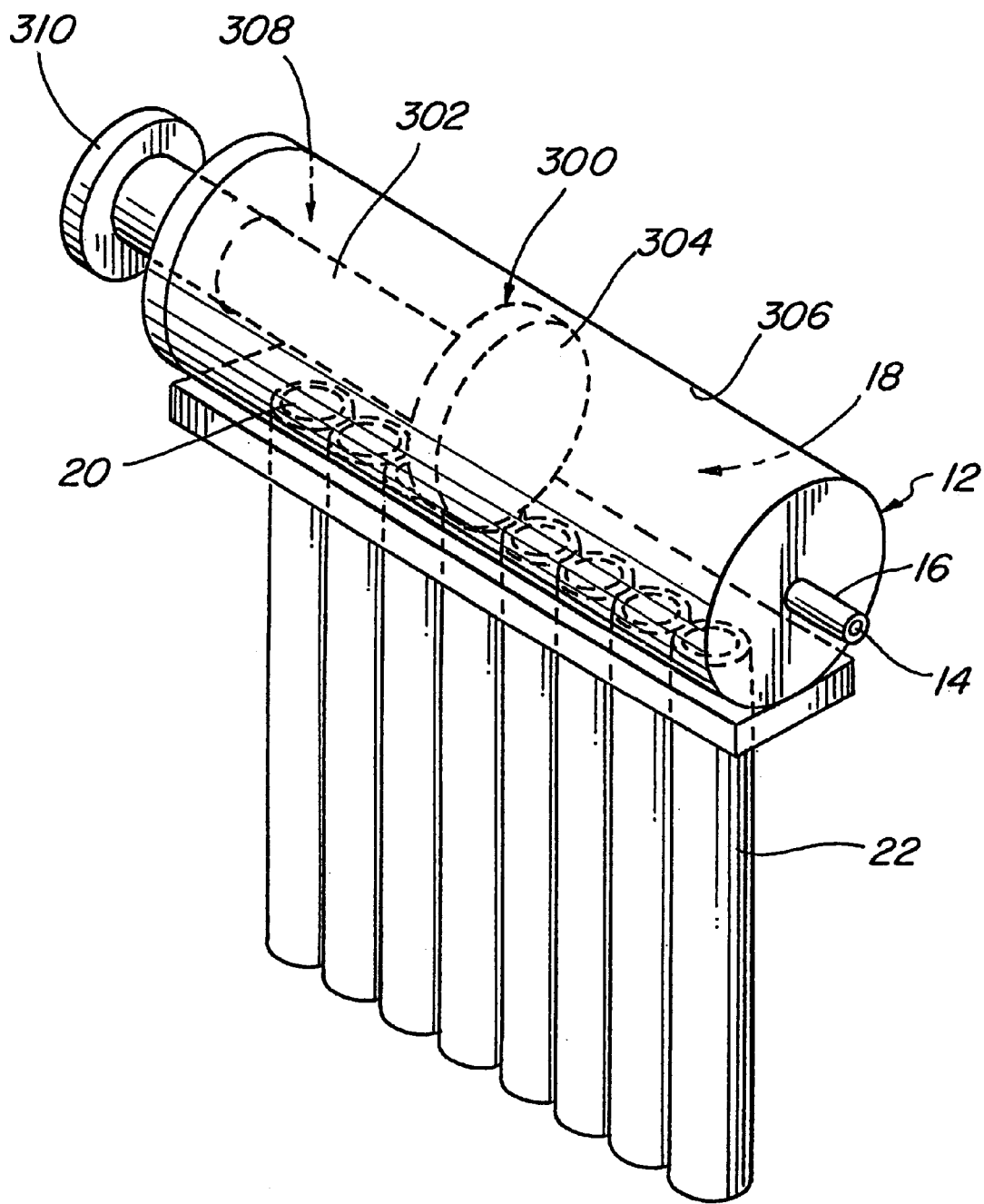
FIG. 3 is an enlarged, fragmentary perspective view of another preferred embodiment of the present invention having a flow control device positioned within the input manifold of the IV fluid heat exchanger.

The IV fluid heat exchanger 10 may utilize any source of heated gaseous fluid as a heating medium, where the IV fluid heat exchanger 10 is positioned in the flow path of heated gaseous fluid traveling into an inflatable, thermal blanket in the preferred embodiment of the present invention. Inflatable thermal blankets are used in hospital settings to control the body temperature of a patient by covering the patient with the blanket and forcing a flow of heated air through the blanket onto the patient. The heated air then passes through apertures in the inner surface of the blanket to flow over the patient. As shown in FIG. 2, the IV fluid heat exchanger 10 may be positioned within the thermal blanket 200 directly in the path of the heated gaseous fluid flowing into the thermal blanket 200. Thermal blanket 200 includes a main chamber 202 serving as a main pathway into which the source of the heated gaseous fluid is input and a plurality of inflatable chambers 204 which are fluidically interconnected with main chamber 202, so that the heated gaseous fluid flows through all of the chambers 202 and 204. While the IV fluid heat exchanger 10 may be positioned within any of the chambers 204 exposed to heated gaseous fluid, the IV fluid heat exchanger 10 is preferably positioned within main chamber 202 where the heated gaseous fluid is directly input and possesses the highest temperature.

The heated gaseous fluid is supplied to thermal blanket 200 from a supply hose (not shown in FIG. 2) extending from a heated gaseous fluid source. Thermal blanket 200 includes a hose mount 206 in main chamber 202 for receiving the supply hose. The center portion 208 is slit to form flaps 210 which are displaced by and engage the supply hose as it is inserted through center portion 208. The perimeter of center portion 208 is also scored to facilitate the bending of flaps 210. Two of the slits extend past the perimeter of center portion 208 to apertures 212 which serve as tube positioning locators for an incoming IV tube 214 and an outgoing IV tube 216 connected to IV fluid heat exchanger 10.

In another preferred embodiment of the present invention, a flow control unit 300 is positioned within input manifold 12 for variably controlling the number of outlets 20 and passageways 22 which are exposed to the flow of IV fluid. By regulating the number of passageways 22 which are open for IV fluid flow, the flow rate of the IV fluid through the IV fluid heat exchanger 10 is regulated. Thus, the surface area of the IV fluid exposed to the inner surfaces of passageways 22 can also be variably controlled to control the amount of heat transferred to the IV fluid from the heated gaseous fluid. The temperature of the fluid is increased by opening more passageways 22 to fluid flow, since a larger surface area of IV fluid is exposed to the higher temperatures of heated passageways 22. The temperature of the heated gaseous fluid surrounding passageways 22 remains relatively constant, wherein the temperature of the IV fluid more closely approaches the temperature of the heated gaseous fluid as more passageways are opened to IV fluid flow. Similarly, when it is only necessary to partially heat the IV fluid, fewer passageways 22 may be opened for IV fluid flow. Thus, the temperature of the IV fluid can be controlled without adjusting the temperature of the heated gaseous fluid.

The flow control unit 300 includes a syringe-type plunger assembly which is reciprocally actuable within input manifold 12 to control the number of passageways 22 accessible by the IV fluid. Flow control unit 300 includes a plunger 302 having a sealing disc 304 at one of its ends which abuts the inner perimeter 306 of intake manifold 12 and prevents the flow of IV fluid between sealing disc 304 and inner perimeter 306. Therefore, sealing disc 304 separates input manifold 12 into two separate chambers, central chamber 18 and fluid-free chamber 308. Central chamber 18 is located between sealing disc 304 and opening 14, and fluid-free chamber 308 is located on the opposite side of sealing disc 304 from central chamber 18. Plunger 302 extends from sealing disc 304 through the surface of input manifold 12 to a handle portion 310 located on the exterior of input manifold 12. Handle portion 310 may be actuated to reciprocally move plunger 302 and sealing disc 304 within input manifold 12, wherein the slidable position of sealing disc 304 determines the number of outlets 20 and passageways 22 accessible by the IV fluid present in central chamber 18. Plunger 302 may include markings indicating the specific IV fluid flow rate achieved by the position of sealing disc 304 based upon the number of passageways 22 open for IV fluid flow. This allows the temperature of the IV fluid to be variably controlled based upon its flow rate, and thus the surface area, of the IV fluid flowing through IV fluid heat exchanger 10. While flow control unit 300 has been described as a syringe-type plunger assembly, it is understood to those skilled in the art that flow control unit 300 may also include other configurations which allow the surface area of the IV fluid exposed to the inner surface of passageways 22 to be variably controlled.

Figure 4:
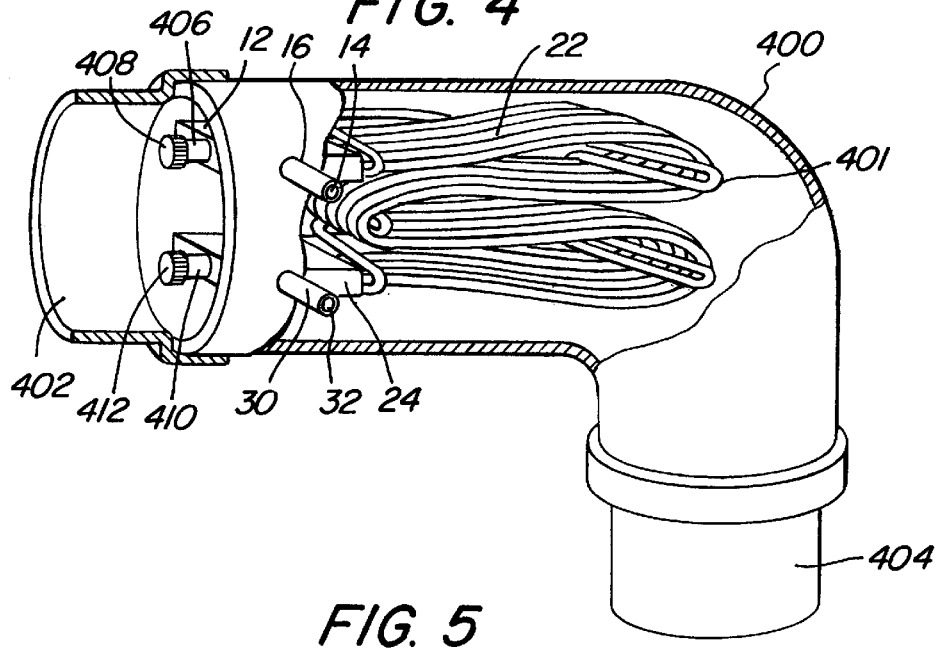
FIG. 4 is a partial cut-away perspective view of an alternative embodiment of the IV fluid heat exchanger of the present invention positioned within a housing which fluidically connects a heated gaseous fluid supply tube to the thermal blanket.
Figure 5:
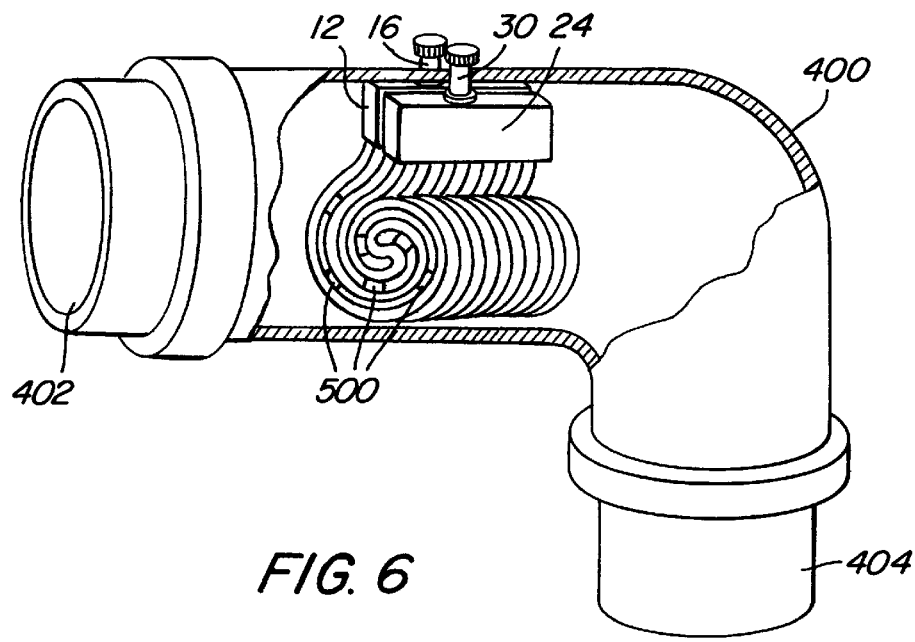
FIG. 5 is a partial cut-away perspective view of yet another alternative embodiment of the IV fluid heat exchanger of the present invention positioned within a housing which fluidically connects a heated gaseous fluid supply tube to the thermal blanket.

As described above, one factor in determining the surface area of the IV fluid exposed to passageways 22 is the length of passageways 22. In order to maximize the amount of heat transferred to the IV fluid, the inner surface area of passageways 22 can be maximized by increasing the length of passageways 22. However, it is also desirable to maintain IV fluid heat exchanger 10 as compact as possible to allow for convenient positioning of the IV fluid heat exchanger 10 in a multitude of possible locations. Accordingly, IV fluid heat exchanger 10 may be formed in a variety of shapes along the longitudinal direction of passageways 22 which maximize the surface area of passageways 22 exposed to the flow of heated gaseous fluid while maintaining a compact shape for the IV fluid heat exchanger 10. This maximizes the amount of heat conducted through passageways 22 to the IV fluid within passageways 22 in a small region. Such shapes include, but are not limited to, a linear shape as shown in FIG. 1, a curved shape as shown in FIG. 2, a serpentine shape as shown in FIG. 4, and a coiled shape as shown in FIG. 5. Further, IV fluid heat exchanger 10 is preferably positioned directly in the flow path of the heated gaseous fluid flowing into the thermal blanket in order to maximize the transfer of heat from the gaseous fluid to the IV fluid, such as within the thermal blanket 200 itself as described in connection with FIG. 2.

Referring now to FIGS. 4 and 5, an alternative embodiment of the present invention will be set forth where the IV fluid heat exchanger 10 is positioned within a housing 400 which fluidically connects the supply tube from the heated gaseous fluid source to thermal blanket 200. Housing 400 includes couplings 402 and 404 attached to opposite ends of housing 400 for connecting housing 400 with the supply tube and hose mount 206 in thermal blanket 200, respectively. Thus, housing 400 allows the gaseous fluid supply tube to be easily connected to thermal blanket 200 without requiring further positioning of the IV fluid heat exchanger 10 within thermal blanket 200. In order to facilitate the connection of housing 400 to both the gaseous fluid supply tube and thermal blanket 200, housing 400 is preferably formed having an angular shape to decrease the positioning requirements of the supply tube with respect to hose mount 206 in thermal blanket 200. The angular shape also allows housing 400 to be rotated about the longitudinal direction of the flow path through coupling 404 in order to accommodate the supply hose from a variety of possible locations. Housing 400 is preferably formed having a 90 degree right angle to further allow the supply hose to be positioned flat against the upper surface of thermal blanket 200.

The IV fluid heat exchanger 10 further includes a supporting structure 401 which provides a framework to maintain passageways 22 in their desired shape for proper heat transfer characteristics. The supporting structure 401 spaces passageways 22 apart during their progression through their desired shape to allow the flow of heated gaseous fluid there between. As shown in FIG. 4, the supporting structure 401 spaces the rows of passageways 22 apart while holding the row of passageways in a serpentine shape. Alternatively, spacers 500 may be positioned between the rows of passageways 22 in order to ensure the separation of the rows of passageways 22 allowing the flow of heated gaseous fluid there between, as shown in FIG. 5 where the coil-shaped embodiment of the IV fluid heat exchanger 10 is illustrated.

In the embodiments of the IV fluid heat exchanger 10 positioned within housing 400, as shown in FIGS. 4 and 5, input protrusion 16 and output protrusion 30 extend through the surface of housing 400 to its exterior to allow input and output IV fluid tubes to be attached respectively thereto. Input manifold 12 may also include at least one other protrusion 406, similar to protrusion 16, extending in a different direction from input manifold 12 than the direction in which protrusion 16 extends. Additional protrusion 406 provides an alternative input source for IV fluid to be delivered to intake manifold 12, thus making intake manifold 12 more versatile in accepting IV fluid sources from various possible locations. When protrusion 406 is not being utilized, a cap 408 is positioned over the opening at the end of the protrusion to prevent the escape of IV fluid from within the input manifold 12 out of protrusion 406. Similarly, output manifold 24 may include at least one other protrusion 410, similar to protrusion 30, extending in a direction similar to protrusion 406 to provide an alternative output path for the IV fluid. A cap 412 is positioned over an opening at the end of the protrusion 410 to prevent the flow of IV fluid from output manifold 24 through protrusion 410 when not being utilized as an output path.

The use of multiple inputs and outputs with the IV fluid heat exchanger of the present invention also allows multiple IV fluids to be heated at the same time for patients requiring more than one IV fluid. In this situation, the input manifold 12 and output manifold 24 may be partitioned into separate chambers for separate IV fluids, where respective passageways 22 interconnecting the separate input and output chambers would be used for the separate IV fluids. Thus, protrusions 16 and 30 could be used as inputs and outputs, respectively, along with a corresponding number of the passageways 22 as a fluid heating path for a first IV fluid, while protrusions 406 and 410 could be used as inputs and outputs, respectively, along with the remaining passageways 22 for a fluid path for a second IV fluid.

Figure 6:
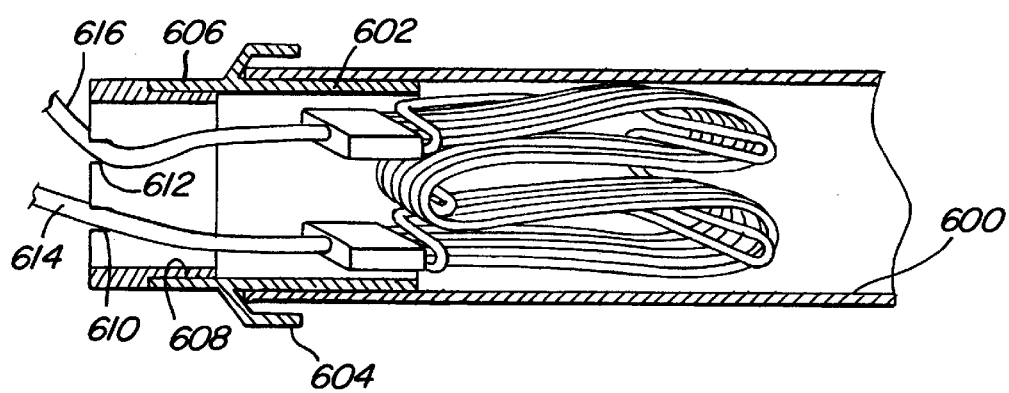
FIG. 6 is a partial cross-sectional view of the IV fluid heat exchanger of FIG. 4 positioned within the heated gaseous fluid supply tube.

Referring now to FIG. 6, another possible arrangement of the IV fluid heat exchanger 10 of the present invention is illustrated where the IV fluid heat exchanger 10 is positioned directly within a supply tube 600 providing a heated gaseous fluid to thermal blanket 200. A supply tube coupling 602 is provided for connection with supply tube 600, where coupling 602 has a diameter smaller than a diameter of supply tube 600. A circumferential flange 604 having a diameter greater than that of supply tube 600 extends in a direction substantially parallel to the body of coupling 602. Supply tube 600 is received for engagement between coupling 602 and flange 604. A second coupling 606, similar to couplings 402 and 404 of FIG. 4, is attached to an opposite end of supply tube coupling 602 from supply tube 600, where a portion 608 of second coupling 606 has a diameter smaller than that of supply tube coupling 602 so as to fit within and engage supply tube coupling 602. Second coupling 606 includes a pair of apertures 610 and 612 for allowing IV tubes 614 and 616, respectively, to enter and exit through the surface of second coupling 606. Apertures 610 and 612 further serve to retain IV tubes 614 and 616 in a desired position.

Figure 7A:
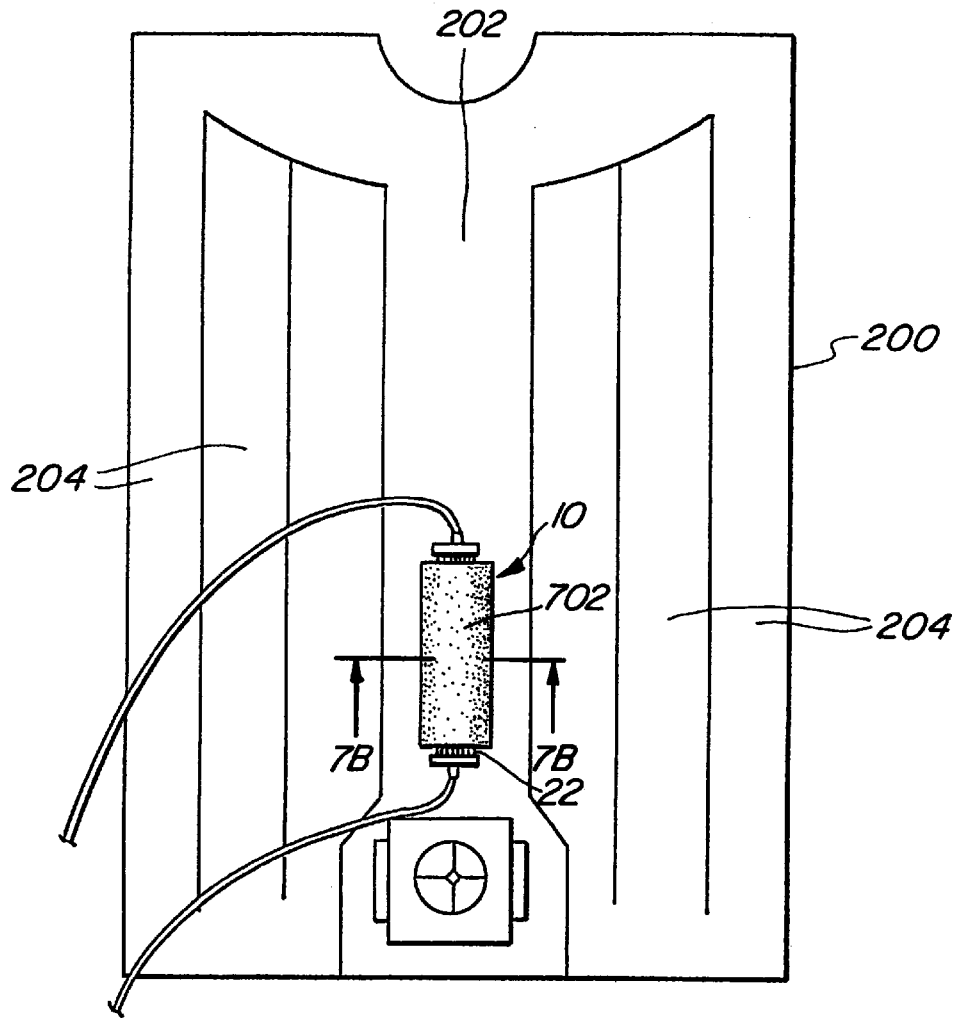
FIGS. 7(A) is a top view of still another alternative embodiment of the IV fluid heat exchanger of the present invention positioned on the outer surface of the inflatable, thermal blanket.
Figure 7B:
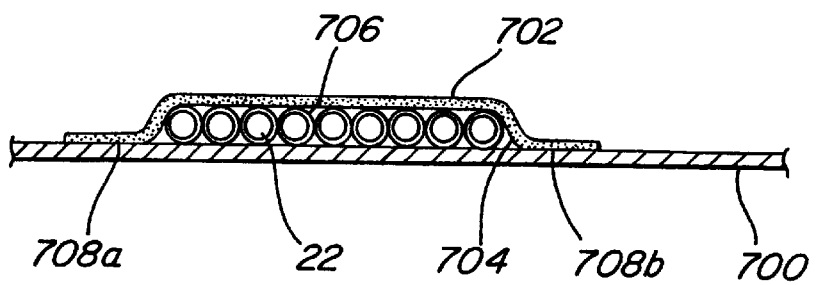
FIG. 7(B) is a cross-sectional view of the IV fluid heat exchanger of FIG. 7(A) taken generally along line VII—VII.

In an alternative embodiment of the present invention, it is further possible for the IV fluid heat exchanger 10 to be positioned adjacent to, but not directly within, the flow path of the heated gaseous fluid. One example of this embodiment is illustrated in FIGS. 7(A) and 7(B), where the IV fluid heat exchanger 10 is positioned on the outer surface of thermal blanket 200 adjacent to the flow path of the heated gaseous fluid through main chamber 202. This embodiment functions equivalently to the IV fluid heat exchanger 10 described in connection with FIG. 1, and, therefore, the function of similarly numbered components will be omitted from the description of this embodiment. The row of passageways 22 is positioned directly on an outer surface 700 of thermal blanket 200 adjacent to main chamber 202. A foam strip 702 having an adhesive bottom surface 704 is adhered to an upper surface 706 of the row of passageways 22. Foam strip 702 is wider than the row of passageways 22 to allow the side ends 708a and 708b to be adhered to outer surface 700 of thermal blanket 200. Thus, foam strip 702 maintains the row of passageways 22 in abutment against outer surface 700 to ensure an efficient transfer of heat from the heated gaseous fluid flowing through main chamber 202 to the IV fluid flowing through passageways 22. Foam strip 702 also provides for thermal insulation of the upper surface 706 of passageways 22 to prevent the escape of heat through the upper surface 706 to the outside atmosphere. In order to provide such insulation, foam strip is preferably formed of an insulating-type closed cell structure. However, it is evident to those skilled in the art that foam strip 702 may be formed of any material or shape which provides the necessary thermal insulation for passageways 22.

Figure 8A:
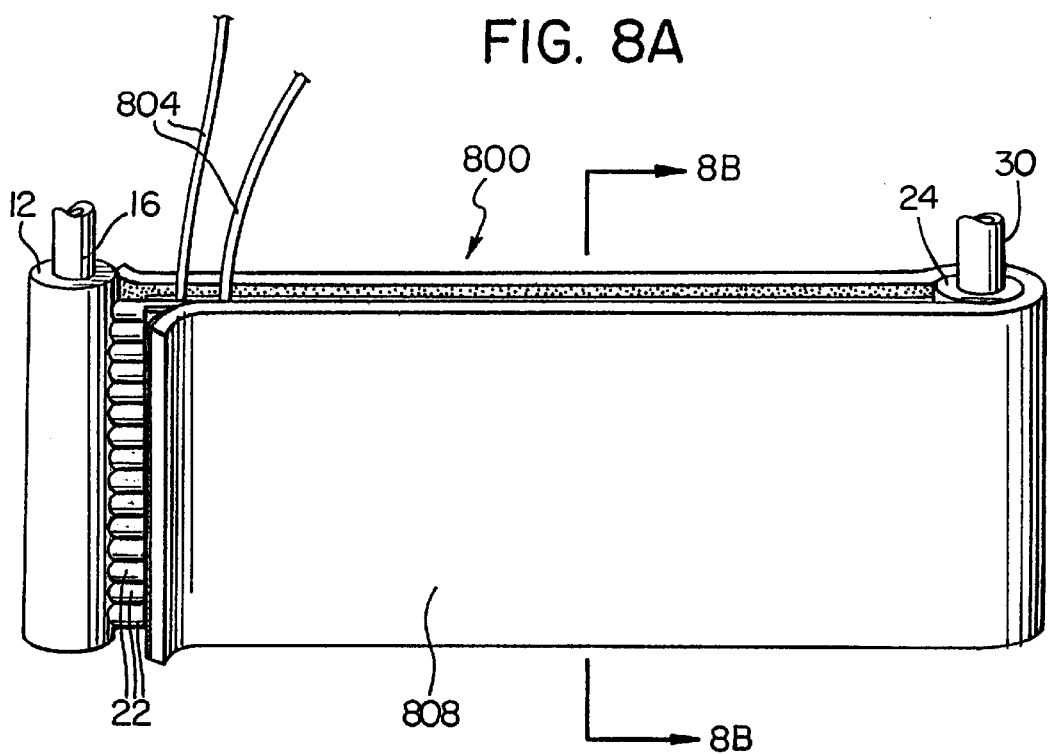
FIG. 8(A) is a partial cut-away perspective view of an alternative embodiment of the IV fluid heat exchanger of the present invention using an electrically-conductive wire as a heating element.
Figure 8B:
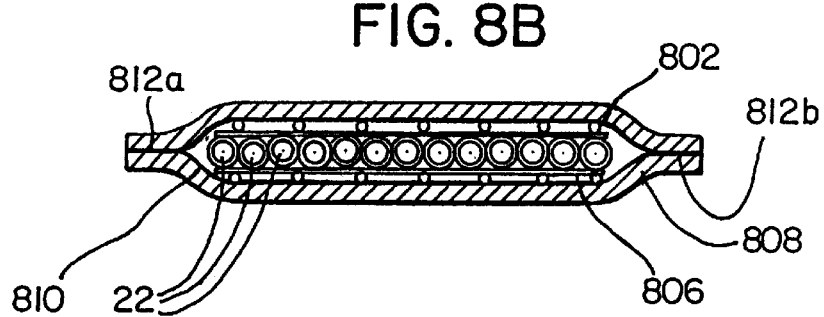
FIGS. 8(B) is a cross-sectional view of the IV fluid heat exchanger of FIG. 8(A) taken generally along line 8B—8B.

The IV fluid heat exchanger 10 of the present invention may alternatively utilize an electrical resistance as the heating source for the IV fluid heat exchanger 10, as shown in the embodiments illustrated in FIGS. 8 to 10. Referring now to FIGS. 8(A) and 8(B), an IV fluid heat exchanger 800 is illustrated having a conductive wire 802 positioned around the exterior of passageways 22. IV fluid heat exchanger 800 functions equivalently to the IV fluid heat exchanger 10 described in connection with FIGS. 1 to 7, and a description of similarly numbered elements will be omitted from the description of this embodiment. Electrical current is introduced into conductive wire 802 through electrical leads 804, wherein the resistance of conductive wire 802 to the current flowing therethrough heats conductive wire 802 and, in turn, the adjacent passageways 22. Electrical leads 804 connect conductive wire 802 to a temperature servocontroller (not shown), which regulates the current flowing through conductive wire 802 to control the temperature of conductive wire 802. Thermisters or similar temperature detecting devices are positioned along conductive wire 802 in order to measure the temperature of conductive wire 802, where the measured temperature is supplied back to the temperature servocontroller through electrical leads 804 for accurate temperature control.

Conductive wire 802 traverses along both sides of passageways 22 in order to expose a larger surface area of passageways 22 to heated conductive wire 802 and efficiently heat the IV fluid flowing through passageways 22. An adhesive material 806 is positioned between conductive wire 802 and passageways 22 in order to retain the positioning of conductive wire 802 in close proximity to passageways 22. Adhesive material 806 is thermally conductive to effectuate the transfer of heat from conductive wire 802 to passageways 22. Adhesive material 806 may be formed from any material having these characteristics, such as a pressure sensitive adhesive tape. A foam strip 808 having an adhesive bottom surface 810 is adhered around the exterior of conductive wire 802 and extends from input manifold 12 along one side of passageways 22, around output manifold 24, and back to input manifold 12 along the other side of passageways 22. Foam strip 808 is wider than the row of passageways 22 to allow side ends 812a and 812b to be adhered together to completely enclose conductive wire 802 and passageways 22. Foam strip 808 functions identically to foam strip 702 in providing thermal insulation to prevent the escape of heat into the surrounding environment as well as protecting passageways 22 and conductive wire 802 from external forces.

Figure 9A:
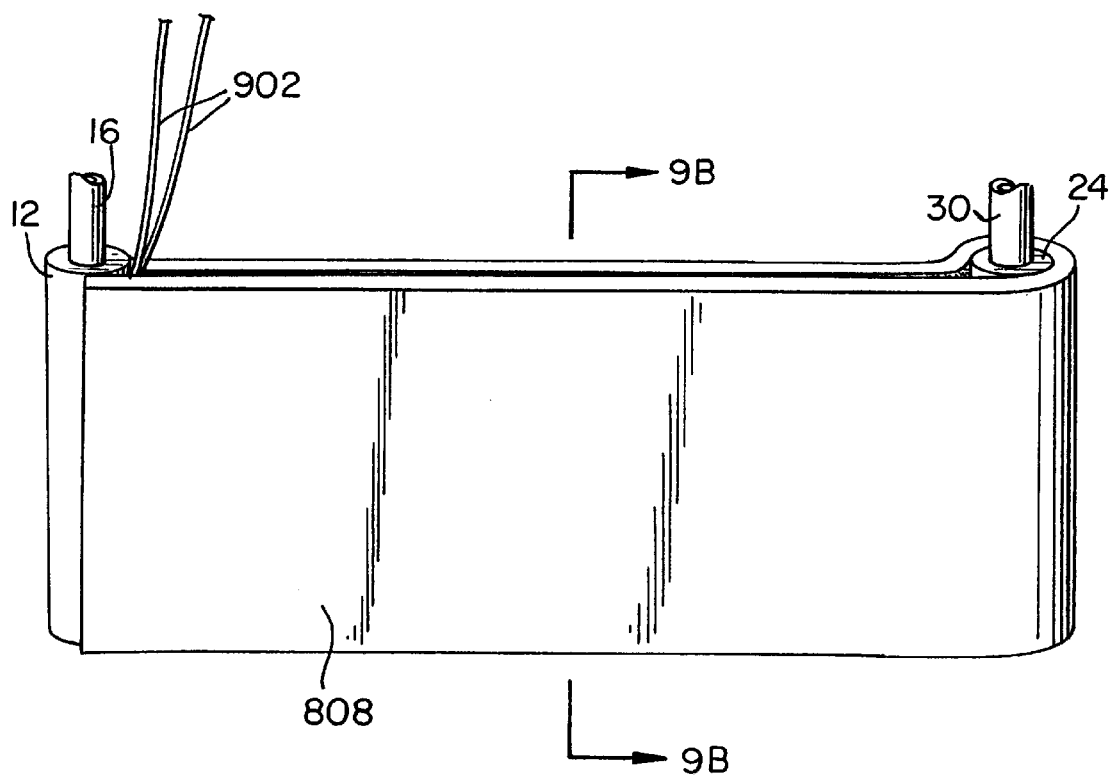
FIG. 9(A) is a partial cut-away perspective view of an alternative embodiment of the IV fluid heat exchanger of the present invention using a coating of electrically-conductive material as a heating element.
Figure 9B:
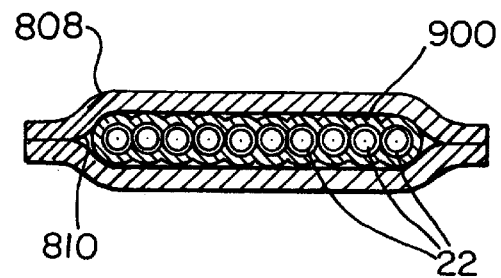
FIGS. 9(B) is a cross-sectional view of the IV fluid heat exchanger of FIG. 9(A) taken generally along line 9B—9B.

Referring now to FIGS. 9(A) and 9(B), an alternative embodiment of the IV fluid heat exchanger 800 of the present invention is shown wherein a coating of electrically conductive material 900 is used as the heating element. Electrically conductive material 900 is formed entirely around the perimeter of the row of passageways 22 to ensure efficient transfer of heat to the IV fluid flowing through passageways 22. Electrical leads 902 introduce current from a temperature servocontroller into electrically conductive material 900, wherein the resistance of electrically conductive material 900 to the current flowing therethrough heats electrically conductive material 900 and, in turn, passageways 22.

Figure 10A:
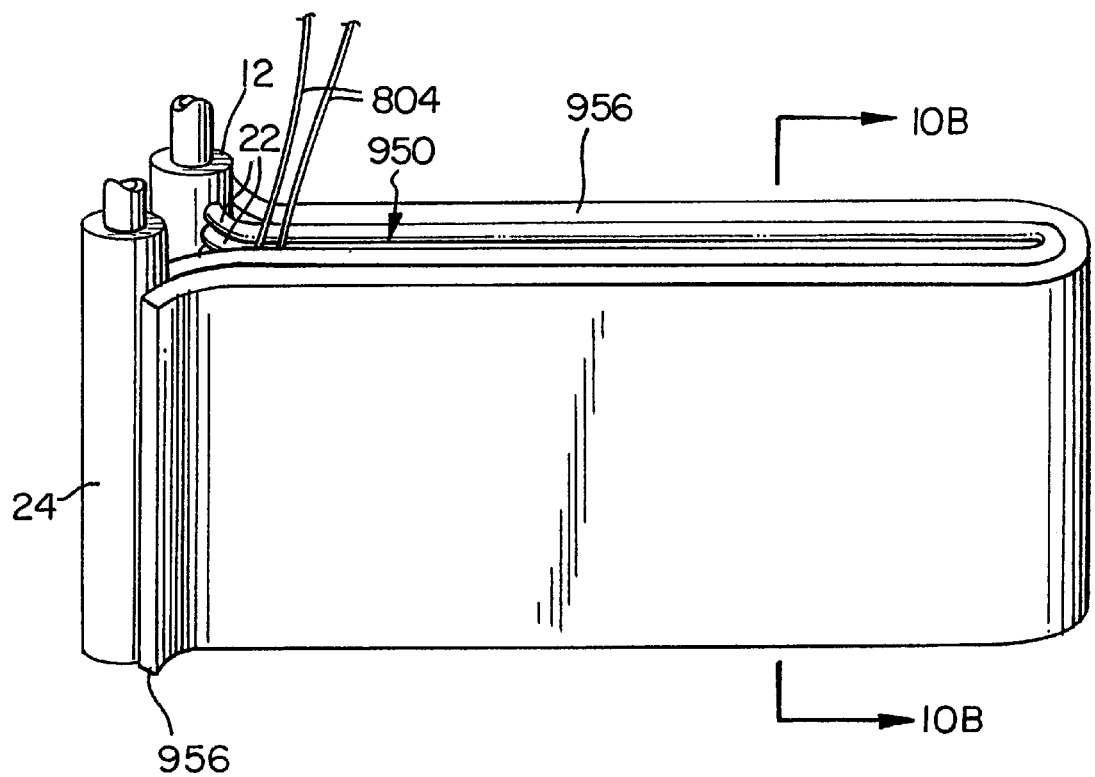
FIG. 10(A) is a partial cut-away perspective view of an alternative embodiment of the IV fluid heat exchanger of the present invention having a reusable electrically-conductive heating element.
Figure 10B:
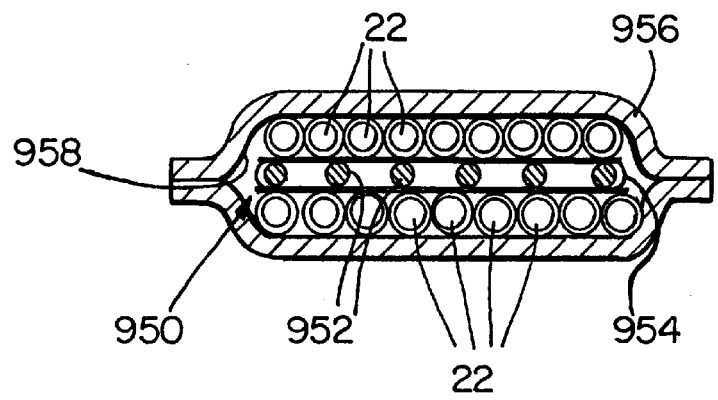
FIGS. 10(B) is a cross-sectional view of the IV fluid heat exchanger of FIG. 10(A) taken generally along line 10B—10B.

The entire IV fluid heat exchanger 800 is preferably discarded after its use. However, a portion of the IV fluid heat exchanger may be constructed to be reusable, as shown in the embodiments of FIGS. 10(A) and 10(B). A heating element 950 having a plurality of electrically conductive wires 952 is constructed to be reusable after each use, where the electrically conductive wires 952 are situated within a thermally conductive housing 954. Housing 954 is preferably formed from a lightweight, thermally conductive plastic or other material having similar characteristics. Passageways 22 are positioned to traverse around both sides of heating element 950 with an adhesive material, similar to adhesive material 806, positioned between housing 954 and passageways 22 in order to retain the positioning of passageways 22 in abutment against heating element 950. Adhesive material 806 and housing 954 are thermally conductive to effectuate the transfer of heat from conductive wires 952 to passageways 22. A foam strip 956, similar to foam strip 808, having an adhesive bottom surface 958 is adhered around the outer surface of passageways 22 to retain passageways 22 in place in abutment against heating element 950.

In each of the above embodiments utilizing electrical resistance as the heating source, the temperature of the IV fluid being warmed can be precisely controlled using the flow control unit 300 positioned with the input manifold 12 to control the surface area of the IV fluid exposed to the inner surfaces of the heated passageways 22. The electrical resistance heating employed in IV fluid heat exchanger 800 allows it to be used independently to warm an IV fluid, so that the IV fluid heat exchanger 800 does not need to be used in conjunction with a thermal heating blanket. Furthermore, the IV fluid heat exchanger 800 may be easily assembled by the user at the hospital or be manufactured in its assembled form shown in FIGS. 8(A) and 8(B).

As can be seen from the foregoing, an IV fluid heat exchanger formed in accordance with the present invention will achieve an optimal amount of heat transfer to an IV fluid by maximizing the surface area of the IV fluid exposed to higher temperatures of a heated gaseous fluid. Moreover, by forming an IV fluid heat exchanger formed in accordance with the present invention, precise temperature control of an IV fluid heated by the IV fluid heat exchanger can be achieved.

In each of the above embodiments, the different positions and structures of the IV fluid heat exchanger 10 of the present invention are described separately in each of the embodiments. However, it is the full intention of the inventors of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An intravenous fluid heat exchanger assembly for transferring heat from a heating medium to an intravenous fluid comprising:

a fluid heat exchanger for receiving the intravenous fluid;

a detachable housing enclosing said intravenous fluid heat exchanger, said detachable housing connectable with a supply tube for providing heated gaseous fluid to a thermal blanket;

an inlet manifold for connecting to a source of intravenous fluid to be heated by the heat exchanger, said inlet manifold having a first inlet nozzle protruding through said housing, and an inlet collecting chamber adjacent said inlet nozzle for collecting said intravenous fluid;

an outlet manifold for connecting a conduit to remove said intravenous fluid from said heat exchanger, said outlet manifold having a first outlet nozzle protruding through said housing, and an outlet collecting chamber adjacent said outlet nozzle for collecting said intravenous fluid; and a plurality of passageways connecting said inlet collecting chamber and said outlet collecting chamber, each of said plurality of passageways being of equal length and directed longitudinally along said housing and stacked at least three levels in a serpentine shape, and each of said plurality of passageways being supported, spaced apart by, and passing around at least three supporting structures mounted internally within said housing, wherein said inlet manifold includes a second inlet nozzle spaced from, and directed along a different direction from, said first inlet nozzle; and wherein said outlet manifold includes a second outlet nozzle spaced from, and directed along a different direction from, said first outlet nozzle.

* * * * *